(12) United States Patent
Pasin et al.

(10) Patent No.: US 9,221,985 B2
(45) Date of Patent: Dec. 29, 2015

(54) SOLVENT COMPOSITIONS

(71) Applicant: TBF Environmental Technology, Inc., Surrey (CA)

(72) Inventors: David Anthony Pasin, Vancouver (CA); López-Arias Diego, Vancouver (CA)

(73) Assignee: TBF ENVIRONMENTAL TECHNOLOGY INC., Surrey, BC (CA)

( * ) Notice: Subject to any disclaimer, the term of this patent is extended or adjusted under 35 U.S.C. 154(b) by 0 days.

(21) Appl. No.: 14/316,835

(22) Filed: Jun. 27, 2014

(65) Prior Publication Data

US 2015/0159028 A1 Jun. 11, 2015

Related U.S. Application Data

(60) Provisional application No. 61/913,746, filed on Dec. 9, 2013.

(51) Int. Cl.
| | | |
|---|---|---|
| C11D 3/43 | (2006.01) |
| C09D 7/00 | (2006.01) |
| C09D 11/033 | (2014.01) |
| A61K 8/37 | (2006.01) |
| A61K 8/69 | (2006.01) |
| C09K 3/00 | (2006.01) |
| A61Q 3/04 | (2006.01) |
| A61Q 3/00 | (2006.01) |
| C11D 7/50 | (2006.01) |

(52) U.S. Cl.
CPC ............ *C09D 11/033* (2013.01); *A61K 8/37* (2013.01); *A61K 8/69* (2013.01); *A61Q 3/00* (2013.01); *A61Q 3/04* (2013.01); *C09D 7/00* (2013.01); *C09D 7/001* (2013.01); *C09K 3/00* (2013.01); *C11D 3/43* (2013.01); *C11D 7/50* (2013.01); *C11D 7/5004* (2013.01); *C11D 7/5018* (2013.01); *C11D 7/5027* (2013.01)

(58) Field of Classification Search
CPC .......... C11D 3/43; C11D 7/50; C11D 7/5004; C11D 7/5018; C11D 7/5027; C09D 7/00; C09D 7/001; C09D 11/033
USPC .......................................... 252/364; 106/311
See application file for complete search history.

(56) References Cited

U.S. PATENT DOCUMENTS

| | | | |
|---|---|---|---|
| 5,244,507 A | 9/1993 | Rowe | 134/38 |
| 6,048,471 A | 4/2000 | Henry | 252/364 |
| 6,187,299 B1 | 2/2001 | Wimmer et al. | 424/61 |
| 6,187,736 B1 | 2/2001 | Jarema | 510/245 |
| 6,706,810 B2 | 3/2004 | Marzouk et al. | 524/599 |
| 7,465,759 B1 | 12/2008 | Salisbury et al. | 523/160 |
| 7,785,413 B2 | 8/2010 | Bortz | 106/311 |
| 8,414,797 B2 | 4/2013 | Howard et al. | 252/364 |
| 8,961,680 B2 * | 2/2015 | Pasin | C09D 7/001 |
| | | | 106/311 |
| 2004/0171755 A1 | 9/2004 | Yokoyama et al. | 525/176 |
| 2011/0140047 A1 | 6/2011 | Howard | 430/270 |
| 2011/0200937 A1 | 8/2011 | Orihara et al. | 430/270 |
| 2011/0275721 A1 | 11/2011 | Carroll et al. | 514/690 |
| 2013/0202893 A1 | 8/2013 | Rihan et al. | 428/423 |
| 2014/0065432 A1 * | 3/2014 | Wuerch et al. | 428/447 |

FOREIGN PATENT DOCUMENTS

| | | |
|---|---|---|
| CA | 2845415 | 5/2014 |
| CA | 2873959 | 12/2014 |
| WO | WO 9842774 | 10/1998 |
| WO | WO 2012/006404 | 1/2012 |
| WO | PCT/CA2014/051182 | 12/2014 |

OTHER PUBLICATIONS

Associations Between Several Sites of Cancer and Occupational Exposure to Benzene, Toluene, Xylene, and Styrene: Results of a Case-Control Study in Montreal, Gerin et al., American Journal of Industrial Medicine, 34, 144-156, 1998.*
Ketone Potentiation of Haloalkane-Induced Hepato- and Nephrotoxicity. I. Dose-Response Relationships, Raymond et al., Jornal of Toxicology and Environmental Health, 45, 465-480, 1995.*
Developemental Toxicity of Inhaled Methyl Ethyl Ketone in Swiss Mice, Schwetz et al., Fundamental and Applied Toxicology 16, 742-748, 1991.*
An effort to test the embryotoxicity of benzene, toluene, xylene, and formaldehyde to murine embryonic stem cells using airborne exposure technique, Shen et al., Inhalation Toxicology, 2009, 21 (12), 973-978.*
Adams, N., Goulding, K. H. & Dobbs, A. J. (1986). Effect of acetone on the toxicity of four chemicals to Selenastrum capricornutum. Bull. Environ. Contam. Toxicol., 36, 254-9.
Altenkirch, H., Stoltenburg, G., & Wagner, H. M. (1978). Experimental studies on hydrocarbon neuropathies induced by methylethyl-ketone (MEK). Journal of neurology, 219(3), 159-170.
Arlien-Soborg, P., (1992). Solvent Neurotoxicity. RC Press, Boca Raton. p. 61-106.
Catoire, L., Paulmier, S., (2006) Estimation of closed cup flash points of combustible solvent blends. Journal of Physical and Chemical Reference Data 35, 9-14.
Freeman JJ, Hayes EP. (1985) Acetone potentiation of acute acetonitrile toxicity in rats. Journal of Toxicology and Environmental Health 15:609-621.
Hansen,CM., (1999) 'Hansen Solubility Parameters: A User's Handbook'. CRC Press LLC, New York Chapter 1, pp. 1-24.
Hare et al. Formulation Strategies Using Exempt Solvents: Latest Developments. Paint & Coatings Industry16.8 (Aug. 2000): 88.
Hewitt, W. R., and Plaa, G. L. (1983). Dose dependent modification of 1,1-dichloroethylene toxicity by acetone. Toxicol. Lett. 16, 145-152.

(Continued)

*Primary Examiner* — Khanh T Nguyen
*Assistant Examiner* — Haidung Nguyen
(74) *Attorney, Agent, or Firm* — Ballard Spahr LLP

(57) ABSTRACT

The present disclosure provides, in part, a solvent composition including methyl acetate and parachlorobenzotrifluoride.

36 Claims, 5 Drawing Sheets

(56) References Cited

OTHER PUBLICATIONS

Hudak, A., & Ungváry, G. (1978). Embryotoxic effects of benzene and its methyl derivatives: toluene, xylene. Toxicology, 11, 55-63.

McMichael, A. J. (1987). Carcinogenicity of benzene, toluene and xylene: epidemiological and experimental evidence. IARC scientific publications, (85), 3-18.

Riihimaki, V., Savolainen, K., 1980. Human exposure to m-xylene: Kinetics and acute eVects on the central nervous system. Ann. Occup. Hyg. 23, 411-422.

Spencer, P. S., & Schaumburg, H. H. (1976). Feline nervous system response to chronic intoxication with commerical grades of methyl n-butyl ketone, methyl isobutyl ketone, and methyl ethyl ketone. Toxicology and Applied Pharmacology, 37(2), 301-311.

Tullo et al. Coatings 98: Solvents Seek a Greener Look Chemical Market Reporter254.15 (Oct. 12, 1998): FR14+.

Examiner's Requisition issued by the Canadian Intellectual Property Office on Jul. 23, 2015 for application CA 2873959, filed on Dec. 8, 2014 (Applicant—TBF Environmental Tech., Inc. // Inventor—Pasin, et al.) (3 pages).

International Search Report and Written Opinion mailed on Mar. 10, 2015 for Patent Application No. PCT/CA2014/051182 filed Dec. 8, 2014 (Applicant—TBF Environmental Technology, Inc.; Inventors—Pasin et al.) (11 pages).

U.S. Appl. No. 61/913,746, filed Dec. 9, 2013, Pasin.

* cited by examiner

SOLVENT COMPOSITIONS

FIELD OF INVENTION

The present disclosure relates generally to solvent compositions. More specifically, the present disclosure relates to solvent compositions that may be used to replace solvents such as xylenes or toluene.

BACKGROUND OF THE INVENTION

Organic solvents, such as acetone, xylene, toluene, and other hydrocarbons or oxygenated solvents are used in a variety of applications. Many of these solvents have toxic and environmentally deleterious properties.

Human and animal studies indicate that exposure to these chemicals can have detrimental effects on the central nervous system, as well as on the hepatic and renal systems.

"Hazardous air pollutants" (or "HAPs"), also known as toxic air pollutants or air toxins, cause or may cause cancer or other serious health effects, such as reproductive effects or birth defects, or adverse environmental and ecological effects. HAPs are regulated in many countries.

Furthermore, many solvents are highly volatile and, of the total amount released to the environment, a significant percentage eventually enters the atmosphere. As such, these solvents have been designated as volatile organic compounds (or "VOCs") and are regulated. Compounds or solvents having lower volatility have been classified as VOC-exempt by many countries.

Toluene and its methylated derivatives m-, o- and p-xylene are aromatic volatile organic compounds (VOCs) used in commercial products such as gasoline, paints, glues and thinners. In addition to these uses, toluene and xylene are abused as neurostimulant agents (Arlien-Soborg, 1992). The neurotoxicity of these solvents (Riihimaki and Savolainen, 1980), as well as their hepatotoxicity (Ungvary, 1990) has been well documented. Chronic studies have also shown reproductive and teratogenic effects (Hudak, 1998: Shen 2009), embryotoxicity (Hudak, 1978), and carcinogenicity (McMichael, 1987; Gerin 1998).

Xylene and toluene are classified as HAP (Harmful Air Pollutants). Approximately 200 chemicals are classified as HAPS for their affects on public health and environment. They cause or may cause cancer or other serious health effects, such as reproductive effects or birth defects, or adverse environmental and ecological effects Furthermore, these solvents are highly volatile and, of the total amount released to the environment, a great percentage eventually enters the atmosphere. Benzene, Toluene, Ethylbenzene, and Xylene (BTEX), account for a third of all VOC's emitted. BTEX are the largest combined group of chemicals that contribute to the formation of deleterious ground-level ozone and photochemical smog.

BTEX solvents have been designated as volatile organic compounds (or "VOCs") or hazardous air pollutants (HAPs) and are regulated in many countries. Compounds or solvents having lower volatility and/or negligible photochemical reactivity have been classified as VOC-exempt by many countries. Such compounds do not participate in the formation of smog or tropospheric ozone, thus regulatory agencies all around the world are promoting their use to avoid the deleterious effects they may cause in the environment and public health. The plastics, coatings and composites industry has been under pressure for some time to reduce HAPs (Hazardous Air Pollutants) and VOCs (Volatile Organic Compounds) in their manufacturing facilities.

Methyl acetate (MA) is a carboxylate ester having the formula $CH_3COOCH_3$. It is flammable liquid which is often used as volatile, low toxicity solvent. Methyl acetate has a solubility of 25% in water at room temperature and is not stable in the presence of strong aqueous bases or aqueous acids. Methyl acetate is VOC-exempt. Methyl acetate can be used as a cleaning solvent or for dissolving resins.

SUMMARY

The present disclosure provides, in part, a solvent composition including methyl acetate (MA) in an amount between about 80% v/v to about 90% v/v; and parachlorobenzotrifluoride (PCBTF) in an amount between about 10% v/v to about 20%.

In some embodiments, the present disclosure provides a solvent composition including essentially MA in an amount between about 80% v/v to about 90% v/v; and PCBTF in an amount between about 10% v/v to about 20%.

In some embodiments, the present disclosure provides a solvent composition including MA in an amount of about 80% v/v; and PCBTF in an amount of about 20%.

In some embodiments, the present disclosure provides a solvent composition including MA in an amount of about 85% v/v; and PCBTF in an amount of about 15%.

In some embodiments, the present disclosure provides a solvent composition including MA in an amount of about 90% v/v; and PCBTF in an amount of about 10%.

In some embodiments, the present disclosure provides a solvent composition for use as a xylene, toluene, PCBTF or TBAc substitute.

In some embodiments, the present disclosure provides a solvent composition that may be a low toxicity solvent composition.

In some embodiments, the present disclosure provides a solvent composition for use as a diluent in the production and manufacture of paints, paint thinners, coatings, adhesives, resins, silicones, or sealants.

In some embodiments, the present disclosure provides a solvent composition for use in short, medium and long oil alkyd resins, epoxy, thermoplastic acrylic, urethane or acrylic urethane formulae.

In some embodiments, the present disclosure provides a solvent composition for use in a coating. The coating may be alkyd, epoxy, vinyl and phenolic coatings, oil-based paints, lacquers, varnishes, or adhesives.

In some embodiments, the present disclosure provides a solvent composition for use in the production of cosmetics. The cosmetics may be perfumes, nitrocellulose based nail polish, methylacrylate monomer based nail polish, or oligonucleotide ("ligomers") based nail polish.

In some embodiments, the present disclosure provides a solvent composition for use in removing nail polishes or preparing the nail for application of nail polishes.

In some embodiments, the present disclosure provides a solvent composition for use as a chemical intermediate.

In some embodiments, the present disclosure provides a solvent composition for use as or in: a diluent in the production and manufacture of paints, paint thinners, coatings, adhesives, resins, silicones, or sealants; a chemical reactant for rubbers, printing or digital inks, dyes, adhesives, lacquers, plastics, cosmetics, pesticides, leather tanners, disinfectants, or explosives; a fullerene indicator; raw material for toluene diisocyanate or trinitrotoluene (TNT); the creation of a solution of carbon nanotubes; a chemical intermediate; a thinner or a cleaning agent; to prepare and clean substrates prior to painting; a cleaner/degreaser, a cleaner for a wide variety of substrates, a surface preparation cleaner (prior to painting); a paint gun and paint line cleaner; to remove inks, adhesives, silicones, resins, paints and coatings from substrates; formulating high solids coatings; organic chemical synthesis; or histological applications.

In some embodiments, the present disclosure provides a kit or commercial package comprising the solvent composition as described herein together with instructions for use as a xylene, toluene, PCBTF or TBAc substitute.

Other aspects and features of the present disclosure will become apparent to those ordinarily skilled in the art upon review of the following description of specific examples in conjunction with the accompanying figures.

BRIEF DESCRIPTION OF THE DRAWINGS

These and other features of the invention will become more apparent from the following description in which reference is made to the appended drawings wherein.

DETAILED DESCRIPTION

Figure 1:
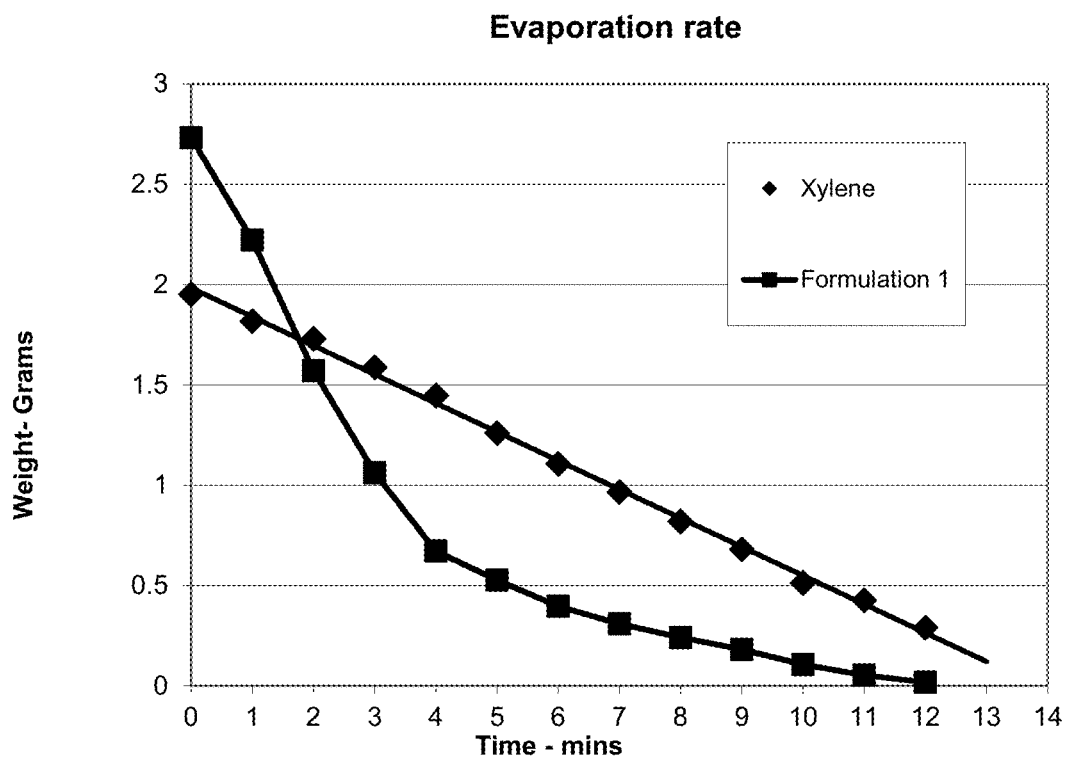
FIG. 1 is a graph showing the evaporation rate of Formulation 1 (squares) vs. xylene (diamonds), as a mixture encompassing the three isomers of dimethylbenzene.

The present disclosure provides, in part, a solvent composition including an acetic acid alkyl (C1-C4) ester (referred to herein as "acetate ester"), such as methyl acetate (MA), ethyl acetate (EA), or tert-butyl acetate (TBAc), and parachlorobenzotrifluoride (PCBTF).

In alternative embodiments, the present disclosure provides, in part, a solvent composition including an acetate ester, such as methyl acetate (MA), or ethyl acetate (EA), where the acetate ester is not TBAc (i.e., a "non-TBAc acetate ester"), and TBAc.

By "acetate ester," as used herein, is meant an acetic acid alkyl ($C_1$-$C_4$) ester having the formula $CH_3CO_2R$, where R is $C_1$-$C_4$ alkyl. "Alkyl" refers to a straight or branched hydrocarbon chain group consisting solely of carbon and hydrogen atoms, containing no unsaturation and including, for example, from one to four carbon atoms, such as 1, 2, 3, or 4 carbon atoms.

In some embodiments, the acetate ester may be present in the solvent composition in any amount between about 55% v/v to about 95% v/v, or about 60% v/v to about 90% v/v, or about 65% v/v to about 85% v/v, or about 70% v/v to about 80% v/v, or any value in between these ranges, for example, about 55%, 60%, 65%, 66%, 67%, 68%, 69% 70%, 71%, 72%, 73%, 74%, 75%, 76%, 77%, 78%, 79%, 80%, 81%, 82%, 83%, 84%, 85%, 90%, 95% v/v, etc.

In some embodiments, the acetate ester may be methyl acetate, which may be present in the solvent composition in any amount between about 55% v/v to about 95% v/v, or about 60% v/v to about 90% v/v, or about 65% v/v to about 85% v/v, or about 70% v/v to about 80% v/v, or any value in between these ranges, for example, about 55%, 60%, 65%, 66%, 67%, 68%, 69% 70%, 71%, 72%, 73%, 74%, 75%, 76%, 77%, 78%, 79%, 80%, 81%, 82%, 83%, 84%, 85%, 90%, 95% v/v, etc.

In some embodiments, the acetate ester may be ethyl acetate, which may be present in the solvent composition in any amount between about 55% v/v to about 95% v/v, or about 60% v/v to about 90% v/v, or about 65% v/v to about 85% v/v, or about 70% v/v to about 80% v/v, or any value in between these ranges, for example, about 55%, 60%, 65%, 66%, 67%, 68%, 69% 70%, 71%, 72%, 73%, 74%, 75%, 76%, 77%, 78%, 79%, 80%, 81%, 82%, 83%, 84%, 85%, 90%, 95% v/v, etc.

In some embodiments, in a solvent composition including PCBTF, the acetate ester may be TBAc, which may be present in the solvent composition in any amount between about 55% v/v to about 95% v/v, or about 60% v/v to about 90% v/v, or about 65% v/v to about 85% v/v, or about 70% v/v to about 80% v/v, or any value in between these ranges, for example, about 55%, 60%, 65%, 66%, 67%, 68%, 69% 70%, 71%, 72%, 73%, 74%, 75%, 76%, 77%, 78%, 79%, 80%, 81%, 82%, 83%, 84%, 85%, 90%, 95% v/v, etc.

In some embodiments, in a solvent composition including the acetate ester, the PCBTF may be present in any amount between about 5% v/v to about 45% v/v, or about 10% v/v to about 40%, or about 15% v/v to about 35%, or about 20% v/v to about 30%, or any value in between, for example, about 16%, 17%, 18%, 19%, 20%, 21%, 22%, 23%, 24%, 25%, 26%, 27%, 28%, 29%, 30%, 31%, 32%, 33%, 34%, 35%, etc.

In some embodiments, in a solvent composition including the non-TBAc acetate ester, the TBAc may be present in any amount between about 5% v/v to about 45% v/v, or about 10% v/v to about 40%, or about 15% v/v to about 35%, or about 20% v/v to about 30%, or any value in between, for example, about 16%, 17%, 18%, 19%, 20%, 21%, 22%, 23%, 24%, 25%, 26%, 27%, 28%, 29%, 30%, 31%, 32%, 33%, 34%, 35%, etc.

In some embodiments, a solvent composition according to the present disclosure includes MA in an amount between about 80% v/v to about 90% v/v; and parachlorobenzotrifluoride (PCBTF) in an amount between about 10% v/v to about 20%.

In some embodiments, a solvent composition according to the present disclosure includes MA in an amount between about 80% v/v to about 90% v/v; and PCBTF in an amount between about 10% v/v to about 20%.

In some embodiments, a solvent composition according to the present disclosure includes MA in an amount of about 80% v/v; and PCBTF in an amount of about 20%.

In some embodiments, a solvent composition according to the present disclosure includes MA in an amount of about 85% v/v; and PCBTF in an amount of about 15%.

In some embodiments, a solvent composition according to the present disclosure includes MA in an amount of about 90% v/v; and PCBTF in an amount of about 10%.

In some embodiments, a solvent composition according to the present disclosure may include more than one acetate ester. For example, a solvent composition according to the present disclosure may include: 60% MA or EA, 30% PCBTF, 10% TBAc.

It is to be understood that varying the concentration of a reagent in a composition will generally require a corresponding adjustment (increase or decrease) in the amount of the other reagents in the composition.

In some embodiments, a solvent composition according to the present disclosure includes an acetate ester, such as MA, EA, or TBAc, in combination with one or more additional reagents to increase dispersion and decrease hydrogen bonding and/or to decrease the polarity of the solvent composition. For example, a solvent composition that resembles the behaviour of xylenes or toluene as a solvent may be formulated using mathematical models to predict the solubility profile of solvent blends. Accordingly, in some embodiments, a solvent composition according to the present disclosure may be formulated according to Hansen solubility parameters (HSP) (Hansen, 1999) and may have: a dispersion parameter ($\delta D$) between about 7.5 and about 9.5; a polarity parameter ($\delta P$) between about 1 and about 4; and a hydrogen bonding parameter ($\delta H$) between about 1 and about 4. In some embodiments, $\delta D$ may be between about 7.5 and about 9; $\delta P$ may be between about 3 and about 4; and $\delta H$ may be between about 2 and about 4. Such parameters result in a Hansen Solubility Parameter ($\delta$ MPa) of about 9.0 to about 10.4, where $\delta^2 = \delta D^2 + \delta P^2 + \delta H^2$. Some embodiments of the solvent composition in the present disclosure include a composition with HSP values similar to that of xylenes or toluene. Additionally, some embodiments of the solvent composition as per to the present disclosure includes a composition in which $\delta P$ and $\delta H$ values which are similar to that of xylenes or toluene.

Table 1 shows parameters of interest for various compounds and compositions.

as hazardous air pollutants (HAPs), as environmentally hazardous, or as ozone-depleting (VOCs).

In some embodiments, a solvent composition according to the present disclosure includes compounds or reagents that are VOC-exempt. "VOC-exempt" means a compound or reagent that has reduced photochemical reactivity (i.e., does not contribute to ozone formation) and has been classified as such by at least one governmental agency, such as the Environmental Protection Agency (EPA) of the United States of America, South Coast Air Quality Management District (SCAQMD-California) or Environment Canada. Such compositions are useful in reducing VOC emissions. MA and PCBTF are presently VOC-exempt.

A compound's maximum incremental reactivity (MIR) value is a measure of the compound's ability to generate ozone due to photochemical degradation. The lower the MIR value, the less ozone (and, accordingly, the less smog) that is generated by the compound. In some embodiments, compositions according to the present disclosure may have a MIR value lower than one or more of xylene (MIR 4.25), toluene (MIR 3.97), TBAc (MIR 0.2) or PCBTF (MIR 0.11). In alternative embodiments, a solvent composition according to the present disclosure may have a MIR value similar to

TABLE 1

|  | Formulation 1* (20% PCBTF - 85% MA) | Formulation 2** (15% PCTBF - 85% MA) | PCBTF | MA | TBAc | Xylenes | Toluene |
|---|---|---|---|---|---|---|---|
| Specific Gravity (@25° C.) | 1.05 | 1.00 | 1.34 | 0.93 | 0.87 | 0.87 | 0.86 |
| Flashpoint (TCC) ° C. | 4 | 4 | 109 | −4 | 16.7 | 17-25 | 16 |
| Boiling Point ° C. | 95 | 70 | 139 | 56 | 98 | 110.6-144 | 135 |
| Appearance | Clear liquid | Clear liquid | Clear liquid | Clear liquid | Clear Liquid | Clear liquid | Clear liquid |
| Viscosity @ 20° C. (mPa · s) cP | 0.47 | 0.45 | 0.79 | 0.37 | 0.7 | 0.34-0.8 | 0.59 |
| $\delta$ (Hansen solubility parameter) hildebrand = 1 cal$^{1/2}$ cm$^{-3/2}$ | 9.17 | 9.18 | 9.15 | 9.5 | 7.77 | 9.36 | 8.88 |
| $\delta D$ (dispersion) cal$^{1/2}$ cm$^{-3/2}$ | 7.82 | 7.76 | 8.8 | 7.6 | 7 | 9.2 | 8.8 |
| $\delta P$ (polar) cal$^{1/2}$ cm$^{-3/2}$ | 3.40 | 3.42 | 2.9 | 3.5 | 1.7 | 1.3 | 0.68 |
| $\delta H$ (hydrogen bonding) cal$^{1/2}$ cm$^{-3/2}$ | 3.37 | 3.46 | 1.9 | 3.7 | 2.9 | 1.15 | 0.98 |
| Surface tension dyn/cm at 20° C. | 24.96 | 25.03 | 25 | 24.8 | 22.4 | 25.32-28.27 | 27.73 |
| Evaporation rate (n-butyl acetate = 1) | 0.9-3.55 | 0.9-5.14 | 0.9 | 6.2 | 2.8 | 0.9 | 1.9 |
| MIR (gO$_3$/gVOC | 0.078 | 0.076 | 0.11 | 0.07 | 0.20 | 4.25-10.71 | 3.97 |
| Solvency (KB value) | 88.75 | 90.30 | 64 | n/a | 114 | 98 | 105 |

*derived from calculations
**direct measurements

Without being bound to any particular theory, the PCBTF may be used to modify the solubility parameters of the acetate ester to, for example, adjust the evaporation rate to that approximating xylene or toluene. In alternative embodiments, and without being bound to any particular theory, the TBAc may be used to modify the properties of the non-TBAc acetate ester to, for example, adjust the evaporation rate to that approximating xylene or toluene.

In some embodiments, a solvent composition according to the present disclosure includes reagents that are not classified methyl acetate (MIR 0.07). In alternative embodiments, a solvent composition according to the present disclosure may have a MIR value of about 0.08. In some embodiments, compositions with low MIR values are useful in aerosol or coating applications. Compositions according to the present disclosure that have suitably low MIR values can, in some embodiments, be mixed with aerosol and coating formulations. The MIR values of the resultant mixtures can be calculated and assessed for their ability to meet reactivity standards, such as those established by the Environmental Protection Agency (EPA) of the U.S.A.

In some embodiments, a solvent composition according to the present disclosure has low volatility (or high flash point). In some embodiments, a solvent composition according to the present disclosure has a higher flash point than xylene (30° C./86° F.). In some embodiments, a solvent composition according to the present disclosure has a flash point of greater than 37° C., for example, 38° C., 39° C., or 40° C. as determined by, for example, Catoire, 2006.

In some embodiments, a solvent composition according to the present disclosure has a flash point of between about 37° C. and 40° C. as determined by, for example, Catoire, 2006. In some embodiments, compositions with a flash point value of greater than 37° C. are considered non-flammable and are therefore useful in applications where flammability is a concern.

In alternative embodiments, a solvent composition according to the present disclosure has a flash point of between about 3.5° C. and 12° C., for example, 3.5° C., 4° C., 5° C., 6° C., 7° C., 8° C., 9° C., 10° C., 11° C., or 12° C., or any value therebetween, as determined by, for example, Catoire, 2006. In general, solvent compositions with higher flash point values may be useful, for example, due to safety considerations although, in some cases, solvent compositions with lower flash points may be used for a variety of industrial applications.

In some embodiments, a solvent composition according to the present disclosure has low toxicity as determined, for example by one or more of oral LD50 on rats, biodegradability, teratogenicity, carcinogenicity and/or hepatic and renal toxicity measurements, which can be determined using standard methods. In some embodiments, a solvent composition according to the present disclosure contains reagents classified as non-carcinogenic.

In some embodiments, a solvent composition according to the present disclosure does not contain substantial amounts of benzene ($C_6H_6$). In some embodiments, a solvent composition according to the present disclosure is substantially free of benzene.

In some embodiments, a solvent composition according to the present disclosure has an evaporation rate approximating that of xylene or toluene at ambient or room temperatures. Evaporation rates can be expressed relative to the evaporation of n-butyl acetate (=1), as a standard. In alternative embodiments, a solvent composition according to the present disclosure has an evaporation rate about 1, 1.5 or 2 times faster than xylene at ambient or room temperatures. In some embodiments, PCBTF may be used as a "tail" solvent to, for example, slow the drying rate of a coating and approximate the evaporation rates of xylene(s) and/or toluene as closely as possible. Without being bound to any particular theory, the "tail" solvent may slow the drying of a coating towards the end, allowing time for it to flow and level, and preventing dry spray, thereby improving the film appearance.

In some embodiments, a solvent composition according to the present disclosure does not leave a residue after evaporation to dryness at, for example, ambient or room temperature.

In some embodiments, a solvent composition according to the present disclosure may be substantially anhydrous, for example, containing less than 0.02 wt % water. In some embodiments, a solvent composition according to the present disclosure contains less than 550 ppm of water. In alternative embodiments, a solvent composition according to the present disclosure contains less than 500 ppm of water.

In some embodiments, a solvent composition according to the present disclosure may be at least partially miscible with water, depending on the ratio of the individual components, such as MA and PCBTF. In some embodiments, a solvent composition according to the present disclosure may be used as a co-solvent in an aqueous coating. Without being bound to any particular theory, such co-solvents may hasten dry time and film formation. In alternative embodiments, a solvent composition according to the present disclosure may include a surfactant or may be used with a surfactant.

In some embodiments, a solvent composition according to the present disclosure is azeotropic.

In some embodiments, a solvent composition according to the present disclosure has a purity of, for example, at least 99.5%, for example, at least 99.6%, 99.7%, 99.8%, 99.9%, or 100%. In alternative embodiments, the acetate ester (such as MA, EA or TBAc), has a purity of, for example, at least 99.5%. In alternative embodiments, the PCBTF, has a purity of, for example, at least 99.5%.

In some embodiments, a solvent composition according to the present disclosure is biodegradable. For example, in some embodiments, solvent compositions according to the present disclosure are readily biodegradable to $CO_2$ and water.

In some embodiments, a solvent composition according to the present disclosure has a high loading capacity, as determined for example by measurements of peak widths at differing loading levels.

In some embodiments, a solvent composition according to the present disclosure has improved flow characteristics, for example, when compared to toluene.

In some embodiments, a solvent composition according to the present disclosure has low viscosity. For example, a solvent composition according to the present disclosure can be 20-25% more efficient in viscosity reduction than toluene.

In some embodiments, a solvent composition according to the present disclosure has improved solvency (kauri-butanol or "Kb" Value) relative to, for example, MA or PCBTF. This may, in some embodiments, permit the use of less solvent when compared to compositions containing xylene or toluene, or containing amounts of PCBTF or MA in amounts greater than solvent compositions according to the present disclosure. In some embodiments, solvent compositions according to the present disclosure have a solvency approximating that of toluene.

In some embodiments, a solvent composition according to the present disclosure has a specific gravity of about 1.

In some embodiments, a solvent composition according to the present disclosure has performance characteristics approximating that of xylene, as described herein or known in the art.

In some embodiments, a solvent composition according to the present disclosure is readily distilled for, for example, recycling.

In some embodiments, a solvent composition according to the present disclosure has a mild odour. In some embodiments, a solvent composition according to the present disclosure does not have an unpleasant and/or strong odour.

In some embodiments, a solvent composition according to the present disclosure can be used to replace one or more of xylene or toluene, or can be used to reduce the amount of TBAc or PCBTF, in various industrial or other applications. For example, a solvent composition according to the present disclosure can be used without limitation as a diluent in the production and manufacture of paints, paint thinners, coatings, adhesives, resins, silicones, sealants, etc. In alternative embodiments, a solvent composition according to the present disclosure can be used to replace one or more of xylene, toluene, TBAc or PCBTF in for example short, medium and long oil alkyd resins, epoxy, thermoplastic acrylic, urethane and acrylic urethane formulae. In alternative embodiments, a solvent composition according to the present disclosure can be used without limitation as a chemical reactant for rubbers, printing or digital inks, dyes, adhesives, lacquers, plastics, cosmetics, pesticides, leather tanners, disinfectants, explosives, etc. In alternative embodiments, a solvent composition according to the present disclosure can be used without limitation as a fullerene indicator or as raw material for toluene diisocyanate (used in the manufacture of polyurethane foam) or trinitrotoluene (TNT) or in the creation of a solution of carbon nanotubes.

A coating, as used herein, may be any fluid composition applied, or for application to, the surface of a substrate to form a thin layer on the substrate. Coatings include, but are not limited to alkyd, epoxy, vinyl and phenolic coatings, oil-based paints, lacquers, varnishes, adhesives, etc. Coatings typically include solvent components and non-solvent components. The solvent components provide the coating with desired fluidity and spreading properties and desired solubility of the non-solvent components. Some or all of the solvent components may evaporate from the substrate surface after the coating is applied, leaving the non-solvent components (such as the pigment of a paint or an ink) on the substrate surface.

In alternative embodiments, a solvent composition according to the present disclosure can be used in the production of cosmetics including but not limited to perfumes, nitrocellulose based nail polish, methylacrylate monomer based nail polish, oligonucleotide ("ligomers") based nail polish, and the like. In alternative embodiments, a solvent composition according to the present disclosure can be used, for example, to remove such nail polishes and, for example, leave the nail bed stain and residue free and/or prepare the nail for application of nail polishes.

In alternative embodiments, a solvent composition according to the present disclosure can be used as a chemical intermediate. For example, a solvent composition according to the present disclosure may be suitable for use as a solvent for fats, oils, waxes, etc. and/or in the formulation and production of various resins.

In alternative embodiments, a solvent composition according to the present disclosure can be used as a thinner or a cleaning agent, or to prepare and clean substrates prior to painting. In alternative embodiments, a solvent composition according to the present disclosure can be used as a cleaner/degreaser, a cleaner for a wide variety of substrates, a surface preparation cleaner (prior to painting), a paint gun and paint line cleaner, etc. In alternative embodiments, a solvent composition according to the present disclosure can be used as to remove inks, adhesives, silicones, resins, paints and coatings from a wide variety of substrates. In alternative embodiments, a solvent composition according to the present disclosure can be used in formulating high solids coatings, for example, to reduce emissions from coating operations.

In alternative embodiments, a solvent composition according to the present disclosure can be used in organic chemical synthesis of, for example, organic resin synthesis, paints or coatings.

In alternative embodiments, a solvent composition according to the present disclosure can be used histological applications, for example, to clean tissue for the preparation of paraffin wax or to prepare very thin slice of tissues for microscopic examination.

It is to be understood that a solvent composition according to the present disclosure can be used in a variety of applications in which xylene, toluene, PCBTF or TBAc are traditionally used, and can be used to replace the xylene, toluene, PCBTF or TBAc in such applications.

Example 1

A solvent composition (Formulation 1) was prepared by mixing the following:

80% (v/v) methyl acetate ≥99% purity (CAS #79-20-9)

20% (v/v) parachlorobenzotrifluoride

Example 2

A solvent composition (Formulation 2) was prepared by mixing the following:

85% (v/v) methyl acetate ≥99% purity (CAS #79-20-9)

15% (v/v) parachlorobenzotrifluoride

In this test, Formulation 1 was found to have the physical/chemical characteristics listed in Table 2:

TABLE 2

| Physical/Chemical Characteristics: | | | |
|---|---|---|---|
| Specific Gravity: (@ 25° C.): | 1.05 | Purity (Wt % Min): | 99.5 |
| Flash Point: (TCC) | 4° C. (39° F.) | Water Content (Wt %): | <0.02% max |
| Initial Boiling: | 95-107° C. (203-225° F.) | Volatility: | 100% |
| Evaporation Rate: (n-Butyl Acetate = 1): | 3.55 | Colour (APHA, Max): | 10 |
| VOC/NPRI Exempt Most Jurisdictions) | | | |

Formulation 1 was a clear liquid with a mild, acetic, fruity non-offensive odour with a calculated MIR value of 0.078.

The evaporation rate of Formulation 1 vs xylene was examined (FIG. 1). Formulation 1 was faster evaporating than xylene by a factor of 1.63-1.65. However it was apparent that the evaporation rate of Formulation 1 slowed towards the end. This slower "Tail" would aid in flow and leveling and help prevent dry spray.

Formulation 1 was evaluated in a fast drying clear speed enamel formula as a replacement for xylene. The added xylene in the control formula (Table 3) was replaced on a volume basis with Formulation 1 (Table 4).

TABLE 3

| | | 1.00 Liters | | |
|---|---|---|---|---|
| ITEM | CODE | MATERIAL | gms | mls |
| 1 | | AB-125/G7794 | 584.25 | 578.47 |
| 2 | | Soya Lecithin TTS | 4.11 | 3.95 |
| 3 | | Bentone 34 | 11.38 | 6.69 |
| 4 | | Methanol | 4.32 | 5.44 |
| 5 | | Water | 0.23 | 0.23 |
| 6 | | Xylene | 15.02 | 17.28 |
| 7 | | Cobalt 12% | 1.23 | 1.19 |
| 8 | | Calcium 10% | 4.69 | 4.74 |
| 9 | | Zirconium 24% | 1.23 | 1.26 |
| 10 | | Glycol Ether EB | 11.97 | 13.27 |
| 11 | | VM&P Naphtha | 108.30 | 142.50 |
| 12 | | Xylene | 179.94 | 207.07 |
| 13 | | Xylene | 14.22 | 16.36 |
| 14 | | Methyl Ethyl Ketoxime | 1.42 | 1.54 |
| | | TOTAL | 942.31 | 1000.00 |

| | Specs | Batch | | |
|---|---|---|---|---|
| Non-Volatile by Wht. % | 33.31 | | | |
| Non-Volatile by Volume % | 24.82 | | | |
| Specific Gravity | 0.94 | | | |
| Cost per Liter | 0.0000 | | | |
| Viscosity, KU | 60-65 | | 20° Gloss | 86.0 |
| P.V.C., % | 2.7 | | 60° Gloss | 96.6 |
| SQ FT/gal @ 1 mil DFT | 398 | | | |
| Hegman Grind | 7 | | VOC | 628.40 |

COMMENTS
Dust Free: 15 mins
Tack Free: 20 mins
Hard Dry: 30 mins

TABLE 4

| | | 1.00 Liters | | |
|---|---|---|---|---|
| ITEM | CODE | MATERIAL | gms | mls |
| 1 | | AB-125/G7794 | 584.25 | 578.46 |
| 2 | | Soya Lecithin TTS | 4.11 | 3.95 |
| 3 | | Bentone 34 | 11.38 | 6.69 |
| 4 | | Methanol | 4.32 | 5.44 |
| 5 | | Water | 0.23 | 0.23 |
| 6 | | Formulation 1 | 17.87 | 17.29 |
| 7 | | Cobalt 12% | 1.23 | 1.19 |
| 8 | | Calcium 10% | 4.69 | 4.74 |
| 9 | | Zirconium 24% | 1.23 | 1.26 |
| 10 | | Glycol Ether EB | 11.97 | 13.27 |
| 11 | | VM&P Naphtha | 108.30 | 142.50 |
| 12 | | Formulation 1 | 214.03 | 207.11 |
| 13 | | Formulation 1 | 16.86 | 16.31 |
| 14 | | Methyl Ethyl Ketoxime | 1.42 | 1.54 |
| | | TOTAL | 981.89 | 1000.00 |

| | Specs | Batch | | |
|---|---|---|---|---|
| Non-Volatile by Wht. % | 31.97 | | | |
| Non-Volatile by Volume % | 24.82 | | | |
| Specific Gravity | 0.98 | | | |
| Cost per Liter | 0.0000 | | | |
| Viscosity, KU | 60-65 | 58.1 | 20° Gloss | 82.5 |
| P.V.C., % | 2.7 | | 60° Gloss | 95.8 |
| SQ FT/gal @ 1 mil DFT | 398 | | | |
| Hegman Grind | 7 | | VOC less Exempt | 543 |

COMMENTS
Dust Free: 10 mins
Tack Free: 15 mins
Hard Dry: 20 mins

The observed results were as shown in Table 5.

TABLE 5

| Properties | Control Formula | Formulation 1 |
|---|---|---|
| Weight Solids, % | 33.31 | 31.97 |
| Volume Solids % | 24.82 | 24.82 |
| Specific Gravity | 0.942 | 0.982 |
| Viscosity, KU | 95.2 | 58.1 |
| Gloss 20°/60° | 86.0/96.6 | 82.5/95.8 |
| VOC g/l minus exempt solvent | 628 | 543 |
| Dust Free, mins | 15 | 10 |
| Tack Free, mins | 20 | 15 |
| Hard Dry, Mins | 30 | 20 |

Accordingly, replacing the additional xylene with Formulation 1 in the control formulation demonstrated that the resultant enamel formula had: lower viscosity, thus allowing formulation at higher volume solids; reduced VOC content; no negative effect on gloss or film appearance; and improved dry times.

In this test, Formulation 2 was found to have the physical/chemical characteristics listed in Table 6:

TABLE 6

| Physical/Chemical Characteristics: | | | |
|---|---|---|---|
| Specific Gravity: (@ 25° C.): | 1.004 | Purity (Wt % Min): | 99.5 |
| Flash Point: (TCC) | 4° C. (39° F.) | Water Content (Wt %): | <0.02% max |
| Initial Boiling point: | 70° C. (170° F.) | Volatility: | 100% |
| Evaporation Rate: (n-Butyl Acetate = 1): | 5.14 | Colour (APHA, Max): | 10 |
| VOC/NPRI Exempt (Most Jurisdictions) | | | |

Formulation 2 was a clear liquid with a mild, acetic, fruity non-offensive odour with a calculated MIR value of 0.076.

Example 3

Comparative Study of Solvency or Reduction Characteristics

Comparative studies were conducted to ascertain the solvency, or reduction characteristics, of Formulation 2 relative to xylene, para-Chlorobenzotrifluoride (PBCTF), and t-Butyl Acetate (t-BuAc). The epoxy resin selected for this study was Momentive's EPON 828, a 100% Bisphenol A based liquid epoxy resin, which is commonly used in formulation of high and ultra-high solids epoxy coatings. The viscosity of EPON 828 epoxy resin was 18000 cps @ 70° F. (21° C.). The viscosity of this epoxy resin, when reduced with xylene, PBCTF, t-Butyl Acetate (t-BuAc), or Formulation 2, at 5% increments down to a solids content of 50% by weight, is shown in Table 7:

TABLE 7

| | Viscosity @ 20 RPM (cps) | | | |
|---|---|---|---|---|
| % Solids Content | Xylene | Formulation 2 | PCBTF | t-BuAc |
| 100 | 18000 | 18000 | 18000 | 18000 |
| 95 | 3350 | 3000 | 5125 | 4250 |
| 90 | 880 | 650 | 1900 | 1150 |
| 85 | 330 | 220 | 1010 | 430 |
| 80 | 148 | 100 | 544 | 192 |
| 75 | 76 | 45 | 278 | 93 |
| 70 | 40 | 28 | 153 | 81 |
| 65 | 28 | 24 | 91 | 26 |
| 60 | 19 | 16 | 52 | 22 |
| 55 | 17 | 13 | 38 | 19 |
| 50 | 13 | 11 | 27 | 15 |

Of the solvents tested, PCBTF is most commonly used in epoxy systems due to its hydrophobic character.

Figure 2:
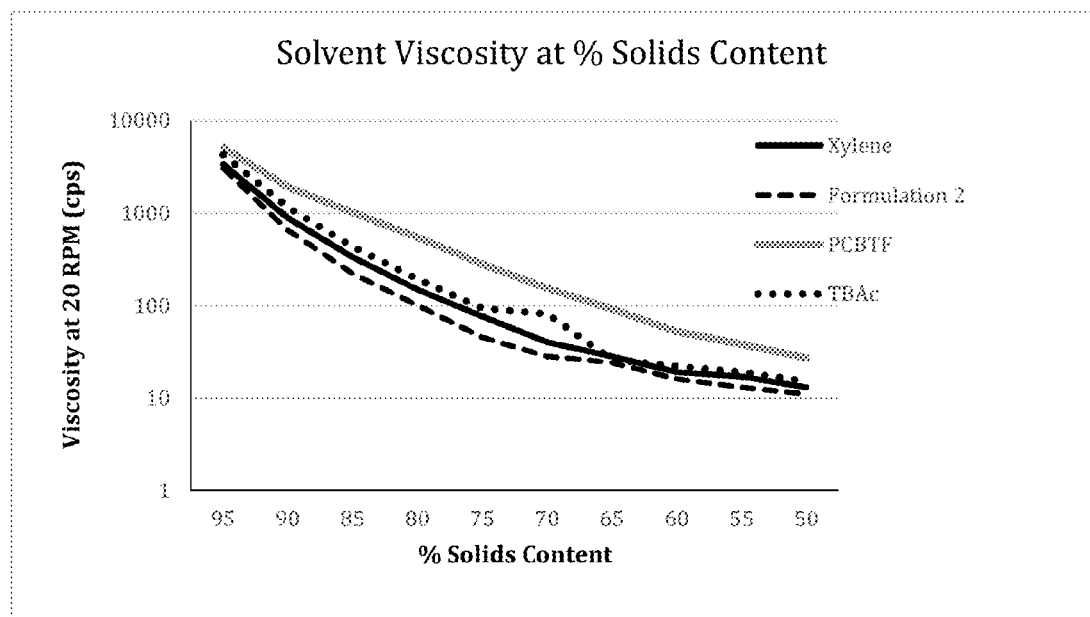
FIG. 2 is a graph showing the solvent viscosity of Formulation 2 as compared with xylene, PCBTF and TBAc.

In this study, Formulation 2 exhibited high solvency with the epoxy resin tested. As shown in Table 7 and FIG. 2, Formulation 2 exhibited faster viscosity reduction than that obtained with xylene or t-BuAc. In addition, Formulation 2 was superior or equal to DMC, depending on the solids level. The reduction characteristics of PCBTF, the most widely used exempt solvent in coatings, exhibited slower viscosity reduction compared to the other solvents tested in this study.

Example 4

Evaluation of the Coating Performance of a 2K Clear Acylic-Urethane Enamel

A 2K high solids clear enamel, based on Dow Chemical's Paraloid AU-750 high solids acrylic polyol and Bayer's Desmodur N-100 isocyanate prepolymer, was formulated with Formulation 2, xylene, PCBTF and TBAc to a total weight solids content of ~78%. The competitive exempt solvents chosen for this evaluation included PCBTF and TBAc, while xylene was utilized as the non-exempt standard for comparison.

Formulations

Each clear coating was formulated with a NCO to OH stoichiometry of 1.1 to 1 on equivalents, with a dibutyltin dilaurate of 0.010% on total resin solids. All formulations were initially prepared with total weight solids of 77.87%. Each formulation was then bulked out to a total coating volume of 100 gallons. A summary of the formulations prepared is shown in Table 8.

TABLE 8

| Material | Pounds per 100 Gallons | | | |
|---|---|---|---|---|
| | Formula # MAJ-2886-1 | Formula # MAJ-2886-2 | Formula # MAJ-2886-3 | Formula # MAJ-2886-4 |
| Part A | | | | |
| Paraloid AU-750 Acrylic Polyol | 554.28 | 562.08 | 575.38 | 554.22 |
| BYK 333 | 3.02 | 3.07 | 3.14 | 3.02 |
| 1% DBTDL Sol'n in MEK | 6.77 | 6.87 | 7.03 | 6.77 |
| Xylene | 75.57 | — | — | — |
| Formulation 2 | — | 76.62 | — | — |
| PCBTF | — | — | 78.43 | — |
| TBAc | — | — | — | 75.55 |
| | 639.64 | 648.64 | 663.98 | 639.56 |
| Part B | | | | |
| Desmodur N-100 Isocynate | 232.86 | 236.12 | 241.73 | 232.82 |
| | 232.86 | 236.12 | 241.73 | 232.82 |
| Total A + B | 872.50 | 884.76 | 905.71 | 872.38 |
| Coating Constants | | | | |
| Stoichiometry NCO to OH) | 1.01 to1 | 1.01 to1 | 1.01 to1 | 1.01 to1 |
| Catalyst Level on resin solids | 0.010% | 0.010% | 0.010% | 0.010% |
| Total Weight Solids | 77.87% | 77.87% | 77.87% | 77.87% |
| Total Volume Solids | 73.41% | 74.44% | 76.20% | 73.40% |
| VOC, g/l | 231.65 | 157.4 | 157.4 | 157.4 |

Substrate Selection & Preparation

The substrate selected for this study was bare aluminum that was primed with a commercial two component, strontium chromate primer. This primed aluminum was selected in an effort to promote good adhesion and flexibility so that any variations in film performance due to solvent selection could be more easily detected.

The strontium chromate primer was applied to a dry film thickness (DFT) of ~1 mil. After 18 hours dry/cure @ R.T., this primed aluminum was topcoated with each of the (4) test coatings. Each topcoat was applied to a DFT of 1.8-2.2 mils.

Performance Testing

The coated panels were allowed to cure for 10 days at room temperature prior to testing, other than periodic checks on gloss and hardness development. At this point, all test coatings were evaluated for the physical coating properties:

| Test Parameter | Test Method |
|---|---|
| Stormer Viscosity | ASTM D562 |
| Brookfield Viscosity | ASTM D2196 |
| Specular Gloss | ASTM D522 |
| Pencil Hardness | ASTM D3363 |
| Dry Film Adhesion | ASTM D3359, method B |
| Wet Film Adhesion | ASTM D3359, method B (modified *) |
| Impact Resistance | ASTM D2794 |
| Mandrel Bend Flexibility | |

Test Results

The physical property test results were as follows.

Acrylic Component Viscosities

Figure 3:
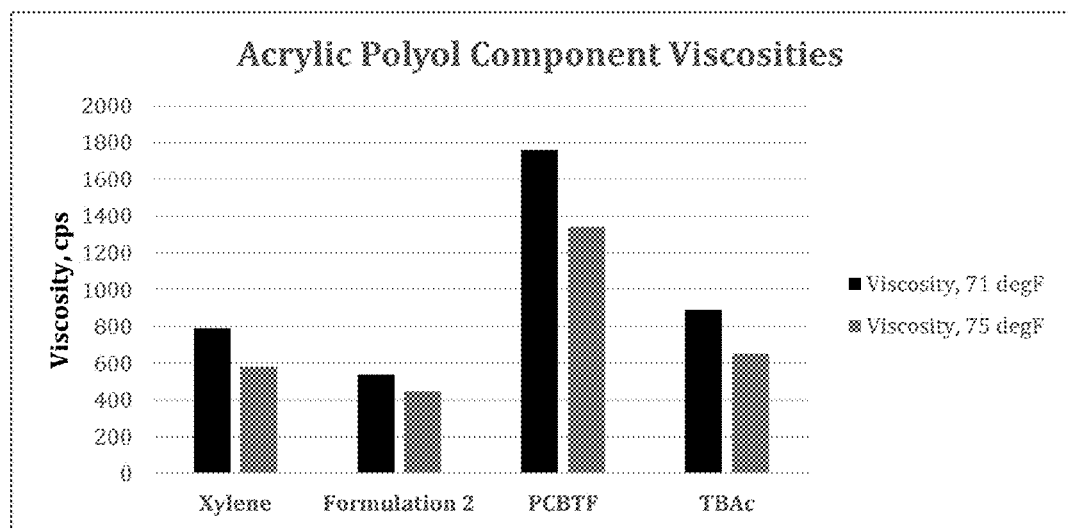
FIG. 3 is a graph showing the acrylic polyol component viscosities of Formulation 2 as compared with xylene, PCBTF and TBAc.

Formulation 2 exhibited the most rapid viscosity reduction of the solvents evaluated (Table 9 and FIG. 3), providing an example of the solvency of Formulation 2 with acrylic polyols. The acrylic components prepared with xylene and t-BuAc yielded comparable viscosities, with each being slightly higher than that of the Formulation 2-based acrylic component. The 2886-3 acrylic polyol with PCBTF yielded the highest component viscosity.

TABLE 9

ACRYLIC POLYOL COMPONENT VISCOSITIES

| Formula No. | Solvent | Viscosity, KU | Viscosity, cps @ 71° F. | Viscosity, cps @ 75° F. |
|---|---|---|---|---|
| MAJ-2886-1 | Xylene | 82 | 790 | 582 |
| MAJ-2886-2 | Formulation 2 | 68 | 540 | 448 |
| MAJ-2886-3 | PCBTF | 97 | 1760 | 1342 |
| MAJ-2886-4 | t-BuAc | 77 | 890 | 654 |

Mixed Coating Viscosities

Figure 4:
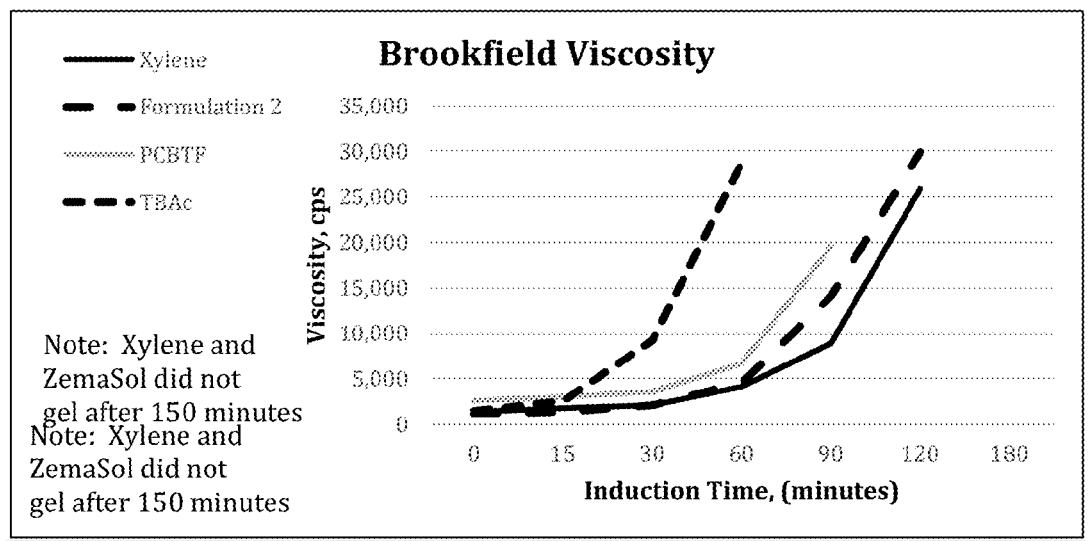
FIG. 4 is a graph showing the mixed coating viscosities of Formulation 2 as compared with xylene, PCBTF and TBAc.

The following is a review of the mixed, or blended, coating viscosities through the pot life of the coating. In Table 10, the viscosities are expressed in Kreb Units (K.U.) and in Table 10, the viscosities are expressed in centipoises (cps). As shown in Tables 9, 10 and FIG. 4, the Formulation 2 prepared coating yielded the lowest fresh coating viscosity, followed closely by xylene and t-BuAc. As seen in acrylic component viscosities, PCBTF also yielded the highest coating viscosity.

TABLE 10

MIXED COATING VISCOSITIES AND POT LIFE TO GELATION

| | Formula Number | | | |
|---|---|---|---|---|
| Induction | MAJ-2886-1 | MAJ-2886-2 | MAJ-2886-3 | MAJ-2886-4 |
| | Solvent | | | |
| Time | Xylene | Formulation 2 | PCBTF | t-BuAc |
| | 1) Stormer Viscosity (K.U.) | | | |
| Initial | 95 | 89 | 112 | 100 |
| 15 min. | 105 | 103 | 121 | 103 |
| 30 min. | 110 | 108 | 125 | 114 |
| 60 min. | 131 | 126 | >141 | 122 |
| 90 min. | >141 | >141 | >141 | >141 |

TABLE 10-continued

MIXED COATING VISCOSITIES AND POT LIFE TO GELATION

| Induction Time | Formula Number | | | |
|---|---|---|---|---|
| | MAJ-2886-1 | MAJ-2886-2 | MAJ-2886-3 | MAJ-2886-4 |
| | Solvent | | | |
| | Xylene | Formulation 2 | PCBTF | t-BuAc |
| 2) Brookfield Viscosity (cps) | | | | |
| Initial | 1340 | 1130 | 2590 | 1450 |
| 15 min. | 1750 | 1320 | 3020 | 2560 |
| 30 min. | 2090 | 2080 | 3560 | 9220 |
| 60 min. | 4130 | 4560 | 6690 | 28750 |
| 90 min. | 8870 | 14960 | 19530 | Soft gel |
| 120 min. | 25900 | 29900 | Soft gel | — |
| 180 min. | Soft gel | Soft gel | — | — |

In review of pot life to gelation, the clear coatings prepared with Formulation 2 and Xylene were the only two solvents to produce a pot life in excess of 2.5 hours. The clear coating prepared with PCBTF yielded a shorter pot life with the formation of a soft gel at 2 hours, while the pot life of the coating prepared with t-BuAc was the shortest of all coatings tested with a pot life of 1.5 hours, after exhibiting a sharp increase in viscosity within 60 minutes after the coating was blended.

Dry Times

Figure 5:
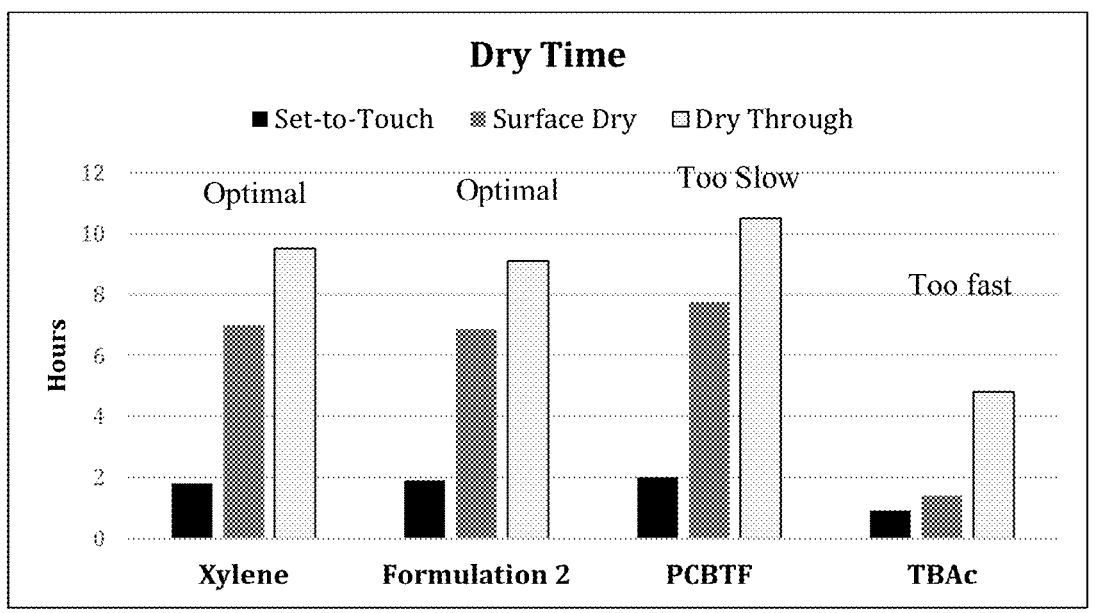
FIG. 5 is a graph showing the dry times of Formulation 2 as compared with xylene, PCBTF and TBAc.

As shown in Table 11 and FIG. 5, the most rapid dry was observed with the coating with TBAc. Formulation 2 exhibited dry times comparable to xylene, with both exhibiting dry-through in 9.0-9.5 hours. The coating with PCBTF was the slowest drying. Based on the results, Formulation 2 offered the best dry profile of the solvents tested in this study.

TABLE 11

DRY TIMES
Dry Film Thickness: 2 mils
Cure Time: 10 days at R.T.
Substrate: Glass
Test Method: ASTM D1640 (circular dry time recorder)

| Stage | Formula Number | | | |
|---|---|---|---|---|
| | MAJ-2886-1 Xylene | MAJ-2886-2 Formulation 2 | MAJ-2886-3 PCBTF | MAJ-2886-4 t-BuAc |
| Set-to-Touch | 1.80 | 1.90 | 2.00 | 0.90 |
| Surface Dry | 7.00 | 6.85 | 7.75 | 1.40 |
| Dry Through | 9.50 | 9.10 | 10.50 | 4.80 |

Specular Gloss

As seen in Tables 12 and 13, the test coatings exhibited excellent gloss, with each producing a 60° gloss and 20° gloss of ~97 and ~93, respectively.

TABLE 12

60° SPECULAR GLOSS
Dry Film Thickness: primer = 1.0-1.5 mils, clear topcoat = 2 mils
Cure Time: 10 days at R.T.
Substrate: Bare Aluminum
Test Method: ASTM D523

| Cure Time | Formula Number | | | |
|---|---|---|---|---|
| | MAJ-2886-1 Xylene | MAJ-2886-2 ZemaSol | MAJ-2886-3 PCBTF | MAJ-2886-4 t-BuAc |
| 24 hours | 98.6 | 98.7 | 98.9 | 98.4 |
| 168 hours | 97.2 | 97.5 | 97.7 | 97.9 |
| 240 hours | 97.1 | 97.5 | 97.7 | 97.8 |

TABLE 13

20° SPECULAR GLOSS
Dry Film Thickness: primer = 1.0-1.5 mils, clear topcoat = 2 mils
Cure Time: 10 days at R.T.
Substrate: Bare Aluminum
Test Method: ASTM D523

| Cure Time | Formula Number | | | |
|---|---|---|---|---|
| | MAJ-2886-1 Xylene | MAJ-2886-2 ZemaSol | MAJ-2886-3 PCBTF | MAJ-2886-4 t-BuAc |
| 24 hours | 93.3 | 93.9 | 94.4 | 93.6 |
| 168 hours | 92.9 | 93.6 | 93.7 | 93.3 |
| 240 hours | 92.9 | 93.6 | 93.5 | 93.3 |

Pencil Hardness Development

In review of the early hardness and hardness development with additional cure, all coatings exhibited a 24 hour hardness of 5B, with the exception of the clear coating prepared with PCBTF which was a 6B. This is suspected to be due to the slow evaporation rate of the PCBTF.

In terms of full cure hardness, the same trend was observed. All coatings with the exception of the clear coating prepared with PCBTF had a hardness of HB as opposed to the B hardness of the clear coating prepared with PCBTF.

TABLE 14

PENCIL HARDNESS DEVELOPMENT
Dry Film Thickness: primer = 1.0-1.5 mils, clear topcoat = 2 mils
Cure Time: 10 days at R.T.
Substrate: Bare Aluminum
Test Method: ASTM D3363

| Cure Time | Formula Number | | | |
|---|---|---|---|---|
| | MAJ-2886-1 Xylene | MAJ-2886-2 ZemaSol | MAJ-2886-3 PCBTF | MAJ-2886-4 t-BuAc |
| 24 hours | 5B | 5B | 6B | 5B |
| 48 hours | 2B | 2B | 2B | 2B |
| 72 hours | 2B | 2B | 2B | 2B |
| 120 hours | 2B | 2B | 2B | 2B |
| 168 hours | HB | HB | B | HB |
| 240 Hours | HB | HB | B | HB |

Coating Adhesion

In this facet of study, the dry and wet film adhesion was determined. Dry adhesion was determined as per ASTM D3359 cross-cut adhesion method, while wet adhesion was measured using a modified version of the ASTM D3359 test method. The procedure for this modified test is as follows:

Cross-hatch is prepared as per ASTM D3359, but no tape pull is performed.

Cover cross-hatch area with cheesecloth and saturate it with de-ionized water.

Allow to stand, undisturbed for 30 min. @ R.T.
Remove cheesecloth and pet dry with a dry towel.
Allow 10 minutes for the film to dehydrate
Perform tape test as per ASTM D3359
Rate adhesion as per ASTM D3359.

As seen in Table 15, the test coatings had excellent dry film adhesion. However, upon testing of the wet adhesion, the top performing coatings were those prepared with xylene or Formulation 2. Each of these coatings had a 4B rating which indicates that 1-5% of the coating lost adhesion The coating prepared with PCBTF had a rating of 3B (5-15% adhesion loss), followed by the coating prepared with t-BuAc rated a 2B (15-35% adhesion loss).

TABLE 15

DRY AND WET FILM ADHESION
Dry Film Thickness: primer = 1.0-1.5 mils, clear topcoat = 2 mils
Cure Time: 10 days at R.T.
Substrate: Bare Aluminum
Test Method: dry film = ASTM D3359, wet film (see attached)

| Formula No. | Solvent | Dry Film Adhesion | Wet Film Adhesion |
|---|---|---|---|
| MAJ-2886-1 | Xylene | 5B | 4B |
| MAJ-2886-2 | ZemaSol | 5B | 4B |
| MAJ-2886-3 | PCBTF | 5B | 3B |
| MAJ-2886-4 | t-BuAc | 5B | 2B |

Coating Flexibility

As shown in Table 16, the flexibility of these test coatings was evaluated for impact flexibility and mandrel bend. As previously noted, the aluminum substrate used for this study was primed with a solvent based strontium chromate epoxy primer to promote adhesion since flexibility will suffer if adhesion is poor. Unfortunately, none of these coatings exhibited good impact flexibility despite the good adhesion values obtained with several of the test coatings. All of the test coatings yielded direct impact flexibility values of 40 in/lbs. This is quite low for most high solids 2K acrylic-urethane enamels. Such coatings will produce a minimum of 100 in/lbs and many reach 160 in/lbs. The "typical" flexibility for coatings based on the Paraloid AU-750 is not known at this time. The test coatings exhibited good mandrel bend flexibility with each passing a ⅛" mandrel after 10 days cure @ R.T

TABLE 16

FLEXIBILITY
Dry Film Thickness: primer = 1.0-1.5 mils, clear topcoat = 2 mils
Cure Time: 10 days at R.T.
Substrate: Bare Aluminum
Test Methods: Impact = ASTM D2794, Mandrel = ASTM D522

| Formula No. | Solvent | Direct Impact | Reverse Impact | Mandrel Bend |
|---|---|---|---|---|
| MAJ-2886-1 | Xylene | 40 in/lbs | <10 in/lbs | Pass ⅛" |
| MAJ-2886-2 | Formulation 2 | 40 in/lbs | <10 in/lbs | Pass ⅛" |
| MAJ-2886-3 | PCBTF | 40 in/lbs | <10 in/lbs | Pass ⅛" |
| MAJ-2886-4 | t-BuAc | 40 in/lbs | <10 in/lbs | Pass ⅛" |

Summary

The results indicated that Formulation 2 exhibited excellent solvency in the polymer system tested, relative to other solvents, as manifested by the relatively low component and coating viscosities. In addition, the coating prepared with Formulation 2 exhibited a pot life equal to that of xylene and superior to coatings prepared with PCBTF and t-BuAc.

Formulation 2 exhibited a dry profile comparable to xylene, and better than T-BuAc and PCBTF.

The coating prepared with Formulation 2: exhibited gloss that was equal or superior to the other coatings tested; produced hardness development equal to xylene and t-BuAc and superior to PCBTF; produced dry and wet film adhesion equal to that of xylene and superior to that of the coatings prepared with PCBTF and t-BuAc; and yielded cured film flexibility equal to that of all other test solvents.

In addition, Formulation 2 and the other exempt solvents tested produced coatings with a VOC of 157.4 g/l as opposed to the 231.6 g/l VOC of the standard coating prepared with xylene. This 32% reduction in VOC is significant, given that the n-butyl acetate in the Paraloid AU-750 acrylic polyol, as supplied, accounts for over 50% of all the solvent in these coatings.

Example 5

Evaluation of the Coating Performance of a Clear Acrylic Enamel

A single component clear enamel, based on Dow Chemical's Paraloid B-66 DMC, was formulated with Formulation 2, xylene, PCBTF, DMC, and t-BuAc to a total weight solids content of ~35%. The Paralod B-66 DMC is a 44.5% solution of the B-66 supplied in dimethyl carbonate (DMC). The competitive exempt solvents chosen for this evaluation included PCBTF, DMC, and t-BuAc, while xylene was utilized as the non-exempt standard for comparison.

Prior to preparation of the test formulations, the Paraloid B-66 DMC was reduced to 40.0% and 35.0% solids with each of the test solvents to determine the viscosity reduction characteristics of each. As shown in Table I, The most rapid reduction in viscosity was obtained with Formulation 2, followed by t-BuAc and DMC.

TABLE 17

VISCOSITY OF PARALOID B-66 DMC ACRYLIC
RESIN 44.5% NV IN DIMETHYLCARBONATE (DMC)
WITH REDUCTION IN SOLIDS WITH XYLENE AND
(3) COMPETITIVE EXEMPT SOLVENTS

| % Non-Volatile | Solvent | | | | |
|---|---|---|---|---|---|
| | DMC | ZemaSol | PCBTF | t-BuAc | Xylene |
| As supplied @ 44.5% | 3110 cps | 3110 cps | 3110 cps | 3110 cps | 3110 cps |
| 40.0% | 970 cps | 760 cps | 1050 cps | 780 cps | 1500 cps |
| 35.0% | 370 cps | 240 cps | 450 cps | 290 cps | 580 cps |

Formulation

The formulations prepared for this study consist solely of the Paraloid B-66 DMC and the solvents selected for this study. No plasticizers or other additives were utilized, thus assuring that any variance in viscosity and/or performance is due solely to the solvent. A summary of the formulations prepared is shown in Table 18.

TABLE 18

| Material | Pounds per 100 Gallons | | | | |
|---|---|---|---|---|---|
| | 2895-1 DMC | 2895-2 ZemaSol | 2895-3 PCBTF | 2895-4 t-BuAc | 2895-5 Xylene |
| Part A | | | | | |
| Paraloid B-66 DMC Acrylic Sol'n | 706.7 | 696.4 | 738.6 | 672.9 | 673.1 |
| DMC | 191.8 | — | — | — | — |
| Formulation 2 | — | 189.1 | — | — | — |
| PCBTF | — | — | 200.5 | — | — |
| TBAc | — | — | — | 182.7 | — |
| Xylene | — | — | — | — | 182.8 |
| | 898.5 | 885.5 | 939.1 | 855.6 | 855.9 |
| Coating Constants | | | | | |
| Weight per Gallon | 8.99 | 8.85 | 9.39 | 8.56 | 8.56 |
| Total Weight Solids | 35.00% | 35.00% | 35.00% | 35.00% | 35.00% |
| Total Volume Solids | 34.44% | 33.94% | 35.99% | 32.79% | 32.80% |
| VOC, g/l | Zero | Zero | Zero | Zero | 376.8 |

Substrate Selection & Application

Each of the test coatings was applied to bare cold rolled steel to a dry film thickness of ~1.8 mils. All coated panels were allowed to cure for 7 days at R.T. prior to any testing other than periodic checks on gloss and hardness development.

Performance Testing

The test coatings were evaluated for the physical coating properties

| Test Parameter | Test Method |
|---|---|
| Brookfield Viscosity | ASTM D2196 |
| Specular Gloss | ASTM D522 |
| Pencil Hardness | ASTM D3363 |
| Dry Film Adhesion | ASTM D3359, method B |
| Impact Resistance | ASTM D2794 |

The following is a review of the data generated for each of the physical properties tested.

Dry Times—

As shown in Table 18, all test coatings exhibited very rapid dry at all stages tested. The most rapid dry was achieved with the coating with t-BuAc, followed closely by Formulation 2 and DMC. Each of these coatings exhibited dry-through in 20 minutes or less. The coating with xylene was next with a dry-through time of 27 minutes, and lastly, the PCBTF at 30 minutes.

Specular Gloss—

All coatings tested dried to a very high gloss with comparable values at both test angles (60° and 20°).

Hardness—

All test coatings, with the exception of the coating with PCBTF, dried to a hardness of 2H after 24 hours @ R.T. No further hardness development was observed over next 6 days, indicating that nearly al of the solvent in this coatings is liberated with the first 24 hours.

Dry Film Adhesion—

Coatings prepared with PCBTF, t-BuAc, and xylene exhibited good adhesion with each exhibiting a rating of 4B, while those prepared with DMC and Formulation 2 exhibited a low rating of 1B. It is suspected that this could change dramatically with the addition of any plasticizer commonly used in thermoplastic acrylic resins.

Impact Resistance—

All test coatings were quite brittle. Only the coating with t-BuAc had over 10 in/lbs of direct impact resistance (12). The lack of flexibility observed may be due to the high Tg of this acrylic and the lack of any plasticizer.

TABLE 19

PHYSICAL PROPERTIES OF CLEAR COATINGS PREPARED @ 35.0% NV WITH PARALOID B-66 DMC ACRYLIC RESIN

| Property | Formula No./Solvent | | | | |
|---|---|---|---|---|---|
| | 2895-1 DMC | 2895-2 Formulation 2 | 2895-3 PCBTF | 2895-4 t-BuAc | 2895-5 Xylene |
| Viscosity @ 20 rpm | 370 cps | 240 cps | 450 cps | 290 cps | 580 cps |
| Dry Times | | | | | |
| Set-to Touch | 5 min. | 4 min. | 5 min. | 3 min. | 6 min. |
| Surface Dry | 16 min. | 15 min. | 30 min. | 11 min. | 22 min. |
| Dry Through | 20 min. | 17 min. | 32 min. | 13 min. | 27 min. |
| 60° Gloss | | | | | |
| 24 hrs. | 118.1 | 119.6 | 117.7 | 118.3 | 117.0 |
| 168 hrs. | 116.9 | 116.4 | 114.8 | 116.0 | 115.1 |

TABLE 19-continued

PHYSICAL PROPERTIES OF CLEAR COATINGS PREPARED @ 35.0%
NV WITH PARALOID B-66 DMC ACRYLIC RESIN

| Property | Formula No./Solvent | | | | |
|---|---|---|---|---|---|
| | 2895-1 DMC | 2895-2 Formulation 2 | 2895-3 PCBTF | 2895-4 t-BuAc | 2895-5 Xylene |
| 20° Gloss | | | | | |
| 24 hrs. | 83.8 | 87.8 | 88.6 | 87.9 | 88.8 |
| 168 hrs. | 82.1 | 82.5 | 85.2 | 80.8 | 82.1 |
| Hardness | | | | | |
| 24 hrs. | 2B | 2B | 2B | 3B | 2B |
| 168 hrs. | 2B | 2B | 2B | 2B | 2B |
| Dry Film Adhesion | 1B | 1B | 4B | 4B | 3B |
| Direct Impact Resistance (in/lbs) | <10 | <10 | <10 | 12 | <10 |

Summary

The results indicated the viscosity of the clear coating with Formulation 2 was the lowest of all solvents tested. In addition, the dry times of the Formulation 2 coating was faster than all other solvents tested with the exception of t-BuAc. However, the evaporation rate of the t-BuAc is so fast that coatings with a high level of t-BuAc cannot be applied via spray since most of this solvent evaporates before the coating ever reaches the substrate, resulting in cobwebbing. This is the same problem that has limited the use of acetone in coatings. Conversely, in most coating systems, the evaporation of the Formulation 2 is fast enough to produce rapid dry without hampering the application.

All solvents tested resulted in very high gloss. This is an indication that all of the solvents tested are quite compatible with the Paraloid B-66 DMC.

All coatings exhibited near equal hardness, and all, with the exception the coating with PCBTF, reached full hardness within the 24 hours after application.

All systems failed to produce flexible films, which may be due to the exclusion of a plasticizer in the test formulations.

REFERENCES

Arlien-Soborg, P., (1992). Solvent Neurotoxicity. RC Press, Boca Raton. p. 61-106.
Catoire, L., Paulmier, S., (2006) Estimation of closed cup flash points of combustible solvent blends. Journal of Physical and Chemical Reference Data 35, 9-14.
C. M. Hansen, (1999) 'Hansen Solubility Parameters: A User's Handbook'. CRC Press LLC, New York.
Gerin, M., Siemiatycki, J., Desy, M., & Krewski, D. (1998). Associations between several sites of cancer and occupational exposure to benzene, toluene, xylene, and styrene: Results of a case control study in Montreal. *American Journal of Industrial Medicine,* 34(2), 144-156.
Hudak, A., & Ungváry, G. (1978). Embryotoxic effects of benzene and its methyl derivatives: toluene, xylene. *Toxicology,* 11, 55-63.
McMichael, A. J. (1987). Carcinogenicity of benzene, toluene and xylene: epidemiological and experimental evidence. *IARC scientific publications,* (85), 3-18.
Riihimaki, V., Savolainen, K., 1980. Human exposure to m-xylene: Kinetics and acute eVects on the central nervous system. Ann. Occup. Hyg. 23, 411-422.
Shen, S., Yuan, L., & Zeng, S. (2009). An effort to test the embryotoxicity of benzene, toluene, xylene, and formaldehyde to murine embryonic stem cells using airborne exposure technique. *Inhalation toxicology,* 21(12), 973-978.

All citations are hereby incorporated by reference.

In the preceding description, for purposes of explanation, numerous details are set forth in order to provide a thorough understanding of the examples. However, it will be apparent to one skilled in the art that these specific details are not required.

The singular forms "a," "an," and "the" include plural referents unless the context clearly dictates otherwise. The endpoints of all ranges directed to the same component or property are inclusive of the endpoint and independently combinable.

The above-described examples are intended to be exemplary only. Alterations, modifications and variations can be effected to the particular examples by those of skill in the art without departing from the scope, which is defined solely by the claims appended hereto.

What is claimed is:

1. A solvent composition consisting essentially of:
   i) MA in an amount of about 80% v/v; and
   ii) PCBTF in an amount of about 20% v/v.
2. A product comprising the solvent composition of claim 1 wherein the product is a xylene, toluene, PCBTF or TBAc substitute.
3. A product comprising the solvent composition of claim 1 wherein the product is a diluent in the production and manufacture of paints, paint thinners, coatings, adhesives, resins, silicones, or sealants.
4. A product comprising the solvent composition of claim 1 wherein the product is a component in short, medium and long oil alkyd resins, epoxy, thermoplastic acrylic, urethane or acrylic urethane formulae.
5. A product comprising the solvent composition of claim 1 wherein the product is a component in a coating.
6. The product of claim 5 wherein the coating is selected from the group consisting of alkyd, epoxy, vinyl and phenolic coatings, oil-based paints, lacquers, varnishes, and adhesives.
7. A product comprising the solvent composition of claim 1 wherein the product is a component in the production of cosmetics.
8. The product of claim 7 wherein the cosmetics are selected from the group consisting of perfumes, nitrocellulose based nail polish, methylacrylate monomer based nail polish, and oligonucleotide (oligomers) based nail polish.

9. A product comprising the solvent composition of claim 1 wherein the product is a nail polish remover or a nail preparation product prior to application of nail polishes.

10. A product comprising the solvent composition of claim 1 wherein the product is chemical intermediate.

11. A product comprising the solvent composition of claim 1 wherein the product is: a diluent in the production and manufacture of paints, paint thinners, coatings, adhesives, resins, silicones, or sealants; a chemical reactant for rubbers, printing or digital inks, dyes, adhesives, lacquers, plastics, cosmetics, pesticides, leather tanners, disinfectants, or explosives; a fullerene indicator; a raw material for toluene diisocyanate or trinitrotoluene (TNT); a component in the creation of a solution of carbon nanotubes; a chemical intermediate; a thinner or a cleaning agent; a substrate preparation cleaner prior to painting; a cleaner/degreaser, a cleaner for a wide variety of substrates, a surface preparation cleaner prior to painting; a paint gun and paint line cleaner; a remover of inks, adhesives, silicones, resins, paints and coatings from substrates; a component in the formulation of high solids coatings; a component in organic chemical synthesis; or a component in histological applications.

12. A kit or commercial package comprising the solvent composition of claim 1 together with instructions for use as a xylene, toluene, PCBTF or tert-butyl acetate (TBAc) substitute.

13. A solvent composition consisting essentially of:
  i) MA in an amount of about 85% v/v; and
  ii) PCBTF in an amount of about 15% v/v.

14. A product comprising the solvent composition of claim 13 wherein the product is a xylene, toluene, PCBTF or TBAc substitute.

15. A product comprising the solvent composition of claim 13 wherein the product is a diluent in the production and manufacture of paints, paint thinners, coatings, adhesives, resins, silicones, or sealants.

16. A product comprising the solvent composition of claim 13 wherein the product is a component in short, medium and long oil alkyd resins, epoxy, thermoplastic acrylic, urethane or acrylic urethane formulae.

17. A product comprising the solvent composition of claim 13 wherein the product is a component in a coating.

18. The product of claim 17 wherein the coating is selected from the group consisting of alkyd, epoxy, vinyl and phenolic coatings, oil-based paints, lacquers, varnishes, and adhesives.

19. A product comprising the solvent composition of claim 13 wherein the product is a component in the production of cosmetics.

20. The product of claim 19 wherein the cosmetics are selected from the group consisting of perfumes, nitrocellulose based nail polish, methylacrylate monomer based nail polish, and oligonucleotide (oligomers) based nail polish.

21. A product comprising the solvent composition of claim 13 wherein the product is a nail polish remover or a nail preparation product prior to application of nail polishes.

22. A product comprising the solvent composition of claim 13 wherein the product is chemical intermediate.

23. A product comprising the solvent composition of claim 13 wherein the product is: a diluent in the production and manufacture of paints, paint thinners, coatings, adhesives, resins, silicones, or sealants; a chemical reactant for rubbers, printing or digital inks, dyes, adhesives, lacquers, plastics, cosmetics, pesticides, leather tanners, disinfectants, or explosives; a fullerene indicator; a raw material for toluene diisocyanate or trinitrotoluene (TNT); a component in the creation of a solution of carbon nanotubes; a chemical intermediate; a thinner or a cleaning agent; a substrate preparation cleaner prior to painting; a cleaner/degreaser, a cleaner for a wide variety of substrates, a surface preparation cleaner prior to painting; a paint gun and paint line cleaner; a remover of inks, adhesives, silicones, resins, paints and coatings from substrates; a component in the formulation of high solids coatings; a component in organic chemical synthesis; or a component in histological applications.

24. A kit or commercial package comprising the solvent composition of claim 13 together with instructions for use as a xylene, toluene, PCBTF or tert-butyl acetate (TBAc) substitute.

25. A solvent composition consisting essentially of:
  i) MA in an amount of about 90% v/v; and
  ii) PCBTF in an amount of about 10% v/v.

26. A product comprising the solvent composition of claim 25 wherein the product is a xylene, toluene, PCBTF or TBAc substitute.

27. A product comprising the solvent composition of claim 25 wherein the product is a diluent in the production and manufacture of paints, paint thinners, coatings, adhesives, resins, silicones, or sealants.

28. A product comprising the solvent composition of claim 25 wherein the product is a component in short, medium and long oil alkyd resins, epoxy, thermoplastic acrylic, urethane or acrylic urethane formulae.

29. A product comprising the solvent composition of claim 25 wherein the product is a component in a coating.

30. The product of claim 29 wherein the coating is selected from the group consisting of alkyd, epoxy, vinyl and phenolic coatings, oil-based paints, lacquers, varnishes, and adhesives.

31. A product comprising the solvent composition of claim 25 wherein the product is a component in the production of cosmetics.

32. The product of claim 31 wherein the cosmetics are selected from the group consisting of perfumes, nitrocellulose based nail polish, methylacrylate monomer based nail polish, and oligonucleotide (oligomers) based nail polish.

33. A product comprising the solvent composition of claim 25 wherein the product is a nail polish remover or a nail preparation product prior to application of nail polishes.

34. A product comprising the solvent composition of claim 25 wherein the product is chemical intermediate.

35. A product comprising the solvent composition of claim 25 wherein the product is: a diluent in the production and manufacture of paints, paint thinners, coatings, adhesives, resins, silicones, or sealants; a chemical reactant for rubbers, printing or digital inks, dyes, adhesives, lacquers, plastics, cosmetics, pesticides, leather tanners, disinfectants, or explosives; a fullerene indicator; a raw material for toluene diisocyanate or trinitrotoluene (TNT); a component in the creation of a solution of carbon nanotubes; a chemical intermediate; a thinner or a cleaning agent; a substrate preparation cleaner prior to painting; a cleaner/degreaser, a cleaner for a wide variety of substrates, a surface preparation cleaner prior to painting; a paint gun and paint line cleaner; a remover of inks, adhesives, silicones, resins, paints and coatings from substrates; a component in the formulation of high solids coatings; a component in organic chemical synthesis; or a component in histological applications.

36. A kit or commercial package comprising the solvent composition of claim 25 together with instructions for use as a xylene, toluene, PCBTF or tert-butyl acetate (TBAc) substitute.

* * * * *